(12) United States Patent
Hein et al.

(10) Patent No.: US 6,334,837 B1
(45) Date of Patent: Jan. 1, 2002

(54) METHOD AND DEVICE FOR TRAINING BODY PARTS OF A PERSON

(76) Inventors: Achim Hein, Gabelsberger Strasse 18, D-91052 Erlangen; Markus Becker, Haardstrasse 37, D-57076 Siegen, both of (DE)

( * ) Notice: Subject to any disclaimer, the term of this patent is extended or adjusted under 35 U.S.C. 154(b) by 0 days.

(21) Appl. No.: 09/554,436
(22) PCT Filed: Nov. 13, 1998
(86) PCT No.: PCT/DE98/03369
 § 371 Date: Jul. 19, 2000
 § 102(e) Date: Jul. 19, 2000
(87) PCT Pub. No.: WO99/25237
 PCT Pub. Date: May 27, 1999

(30) Foreign Application Priority Data

Nov. 14, 1997 (DE) ........................................ 197 50 441

(51) Int. Cl.$^7$ ............................................. A61B 5/103
(52) U.S. Cl. .............................. 482/8; 482/9; 600/595
(58) Field of Search ................................. 482/1–9, 900, 482/902; 600/587, 595; 73/379.01, 379.08

(56) References Cited

U.S. PATENT DOCUMENTS

| 4,633,237 | A | | 12/1986 | Tucknott et al. |
| 5,375,610 | A | | 12/1994 | LaCourse |
| 6,095,991 | A | * | 8/2000 | Krausman et al. .......... 600/595 |
| 6,119,516 | A | * | 9/2000 | Hock ...................... 73/379.01 |

FOREIGN PATENT DOCUMENTS

| DE | 40 21 240 | 1/1992 |
| DE | 32 48 179 | 6/1994 |
| EP | 0 211 984 | 3/1987 |
| WO | 91/11218 | 1/1991 |

\* cited by examiner

*Primary Examiner*—Glenn E. Richmon
(74) *Attorney, Agent, or Firm*—Browdy and Neimark

(57) ABSTRACT

The invention relates to a method for training body parts of a person in a sitting position, by preselecting a desired movement and generating movement signals form a movement of a sitting person, via a sensor unit.

24 Claims, 10 Drawing Sheets

METHOD AND DEVICE FOR TRAINING BODY PARTS OF A PERSON

CROSS REFERENCE TO RELATED APPLICATION

Figure 1:
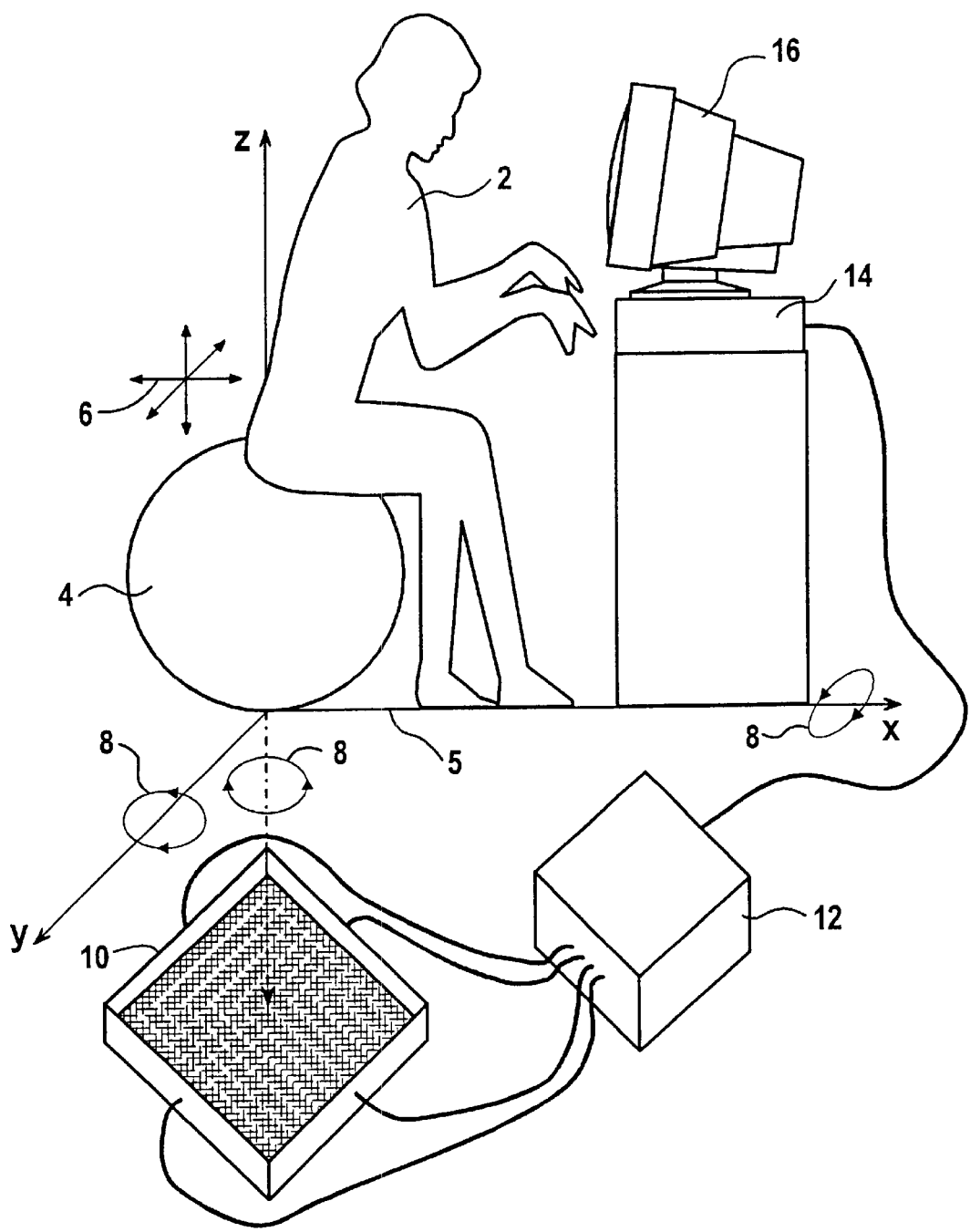

The present application is the national stage under 35 U.S.C. 371 of PCT/DE98/03369, filed Nov. 13, 1998.

The invention relates to a method and a device for training body parts of a person in a sitting position.

Posture damages are generally diagnosed by a physician and treated with physical therapy by an appropriate practitioner. After a given damage has been diagnosed, it is attempted with rehabilitation measures to stabilize the locomotor system as appropriate. However, attempts already exist to recognize corresponding characteristics by means of automated methods and then eliminate same. This includes, in particular, methods which measure recorded data from movements of the arms, legs or the head. The movement sequences can then be evaluated, after the actual movement activity, by means of various differently implemented analyses.

It is also known, for the operation of computer-aided applications such as a text processing software, to use foot or head operated input devices besides the keyboard and mouse. These attempts are directed towards optional operating options as substitutes for hand-controlled operations.

From DE-OS 39 39 327 a method is known for improving a damaging posture, as well as a measuring device and item of clothing for implementing the inventive method. With these, the body is forced, through an asymmetric load, to take a normal posture. The angle of inclination of lines is measured that connect body parts characteristic for a person's posture.

From the German utility-model patent 297 12 990 a recognition and warning system for bad sitting postures is known, which issues a warning sound when a user's head moves too closely to a surface. This is done by evaluating the amount of coverage of a light sensor by the head.

The German utility model 296 12 724 describes a device for computer-aided balance therapy with a ball section, which has an enlarged cut surface as a standing platform for persons. A control of a computer program takes place by means of built-in switches. The ball section is anchored centrally inside a switch holder ring so that it is movable in all lateral directions. The switches that are located in the switch holder ring can be actuated by shifts in the person's balance. The switching operation causes a monitor cursor to be moved in corresponding directions.

DE-OS 40 21 240 describes a device for checking the posture of persons during their use of training equipment, seats or the like. The device comprises at least one pressure sensitive sensor element, a carrying element for the sensor element or elements and an evaluation unit. The carrying element can be attached to the respective training equipment, seat or the like in such a manner that the person, in dependence on the person's posture, exerts a certain pressure on the sensor element or elements. The output signals of the sensor elements are applied to the evaluation unit. The evaluation unit comprises a display unit, which shows the posture currently taken by the person.

A device for the functional and quantified evaluation of the human activity is described in the U.S. Pat. No. 5,375,610. The device comprises four main components: a data acquisition unit, a body suit interface, a body suit with a multitude of switches and a graphically oriented software package. The switches are arranged on the body suit in such a manner that they can acquire the movements that are to be measured. Graphical analysis means can be connected to the sensors via data acquisition means. The graphical analysis means provide, by means of match stick men, a visual presentation of body and arm positions across time in real time. This may be used as movement feedback. The various postures can, furthermore, be illustrated on the monitor with the aid of match stick men. For this purpose the user selects the posture to be shown from a list.

In the state of the art described below, the efforts are targeted at optimized operating means for a computer that are equivalent to hand-operated controls.

In WO96/01448 a control device for computers or industrial processes is described. The concept is based on the principle of controlling a computer through movements of the body, which are transmitted via the chair. The control device is characterized in that a plurality of transducers are built into a chair. A first transducer is provided to detect turning movements of the chair. It transmits signals that correspond to movements in the horizontal direction. A further transducer detects movements in the vertical direction. The output signals of the transducers are routed to a transmitter via an interface. In this manner a conventional mouse can be completely or partly replaced by movements of the chair. Turning movements, for example, activate a cursor on a display unit in the horizontal direction, whereas back and forth movements of the body move the cursor in the vertical direction.

In the German utility model 297 04 478 a device is described for the operation of a joystick by a standing or sitting operator. A horizontally arranged plate is mounted above a joystick that is to be operated so that the plate is tiltable and movable. On its underside, an operating mechanism is provided for the lateral movement of the joystick, which operates the joystick when the plate is tilted. An operator stands or sits on this plate and shifts his body weight, which results in a tilting of the plate, thus in the operation of the joystick and thus, in turn, in the desired interaction with a game or a virtual world.

In the U.S. Pat. No. 4,843,538 a device and process are described by which a real time control of computer events can be performed via an image of a human body. This is done with a perception and characteristics analysis.

The invention is now based on the object of presenting a method and a device for training body parts of a person in a sitting position whereby body movements can be detected and controlled.

The first object is met, with respect to the method, with the following procedure steps:
  specification of a desired movement,
  generation of movement signals from a movement of a sitting person by means of a sensor unit, and
  generation of a presentation of the movement from the movement signals on a monitor.

This permits the display, monitoring and correction of body movements and postures, particularly also bad postures. The sensory monitoring and the display permit a qualified guiding of movements. For example, a special movement program may be specified that has been developed by a physician for a certain problem, for rehabilitation purposes. The monitoring of the movement program is carried out automatically via the sensor technology without a need for a long-lasting presence of a trained practitioner.

A further advantage of the invention lies in the fact that known problems in the posture and locomotor system in the continuously expanding area of personal computer jobs can be improved by means of the additive or also optional use of the invention. The user may be prompted, either permanently or for limited periods of time, for example by means of a back relaxation software, to use the movement-activating input system. This option would prophylactically counteract the loss of mobility and the curvatures of the spine seen in this line of work.

Furthermore, the possibility exists to set up virtual rehabilitation worlds, in which, e.g., a physician or therapist specifies a movement to a therapy group. The protocol of the movement can additionally be transmitted to the physician or therapist. For control purposes the participants in the therapy group can monitor the presentation of the movement on a monitor, like in a mirror.

An advantageous embodiment is characterized in that the desired movement is specified in the form of a desired path, which a cursor is to follow on the monitor. Specifying a desired path permits a targeted therapeutic guidance of movements.

In a further advantageous embodiment of the invention, the movement of the person is transmitted to the sensor unit via a seat device. In this manner various seat devices may be used that have been developed under therapeutic aspects.

A further advantageous embodiment is characterized in that a quality signal is formed from the desired movement and the movement signals, as a measure for the correspondence between the desired movement and the movement. The quality signal provides the patient with feedback on the overall success of the therapeutic movements that were just performed. A therapeutic quality measure is thus introduced, which may serve for the comparability of different persons or also for different training units for one person.

The movement signals are preferably detected and presented quasi-continually. Quasi-continually, in this context, means that, with digital signal processing, the scanning rate for a conversion of the* into a digital format of the movement signals, which are generally initially present in analog form, is so high that an observer gains the impression of a continuous acquisition and presentation.

*Translator's note: this is a literal translation of the respective part of the German sentence, which is either incomplete or contains an extraneous "of the" (German "der").

The second object, with respect to the device, is met with the combination of the following characteristics means for specifying a desired movement, a sensor arrangement for generating movement signals from a movement of a sitting person, a processing unit that is connected to the sensor arrangement for generating a presentation of the movement from the movement signals, and a monitor that is connected to the processing unit for a visualization of the presentation.

The resolution of the sensor elements corresponds to the resolution of a monitor of e.g., approximately 1200×800 pixels. The movement signals may be routed to the processing unit after they have been processed in an analog or also digital form.

An advantageous embodiment is characterized in that a seat device is connected to the sensor arrangement for transmitting forces to the sensor arrangement that are generated by the movement of the sitting person. This permits a normal basic posture to be taken during its use.

The seat device may be designed as a chair or stool. In a particularly advantageous design a ball seat is used as the seat device. Ball seats are medically recognized for the therapy of posture damages, and furthermore convert the body movement into easily detected rolling motions.

In a further advantageous design the sensor arrangement comprises a multitude of sensor elements arranged on a surface. With these, the movement of a ball seat lying on same can be measured by the shifting of the imprint of the ball seat on the sensor arrangement. The sensor elements detect the movement, for instance by pressure sensitivity, distance sensitivity or path sensitivity, rotation sensitivity, speed sensitivity or acceleration sensitivity. The sensor arrangement may be designed, e.g., as an appropriately sensitive mat. The sensor principles may be electrical, magnetic, optical or also mechanical receptors, such as light barriers, piezo sensors, Hall sensors, etc. Further designs of the invention are characterized by the subclaims.

Figure 2:
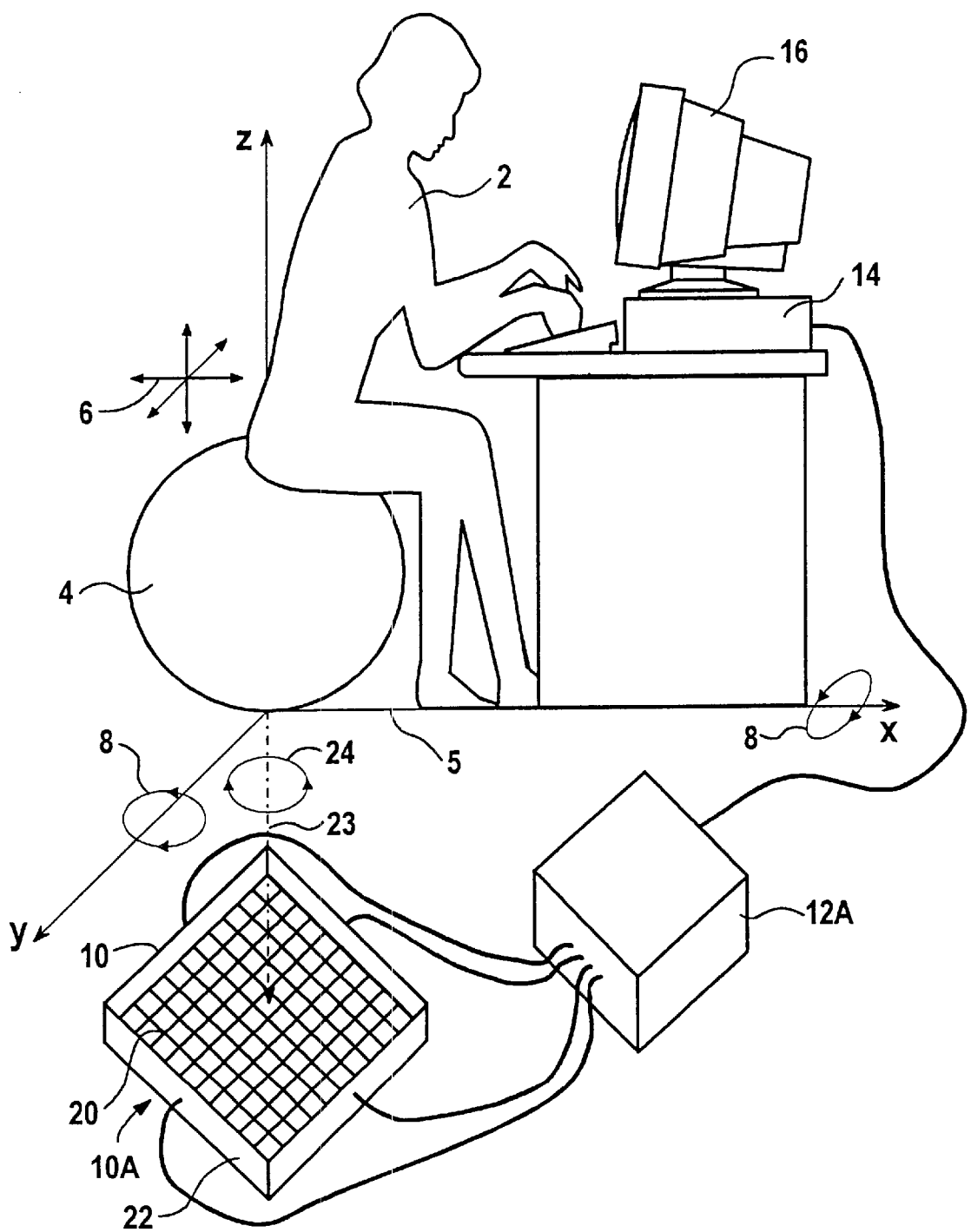
Figure 3:
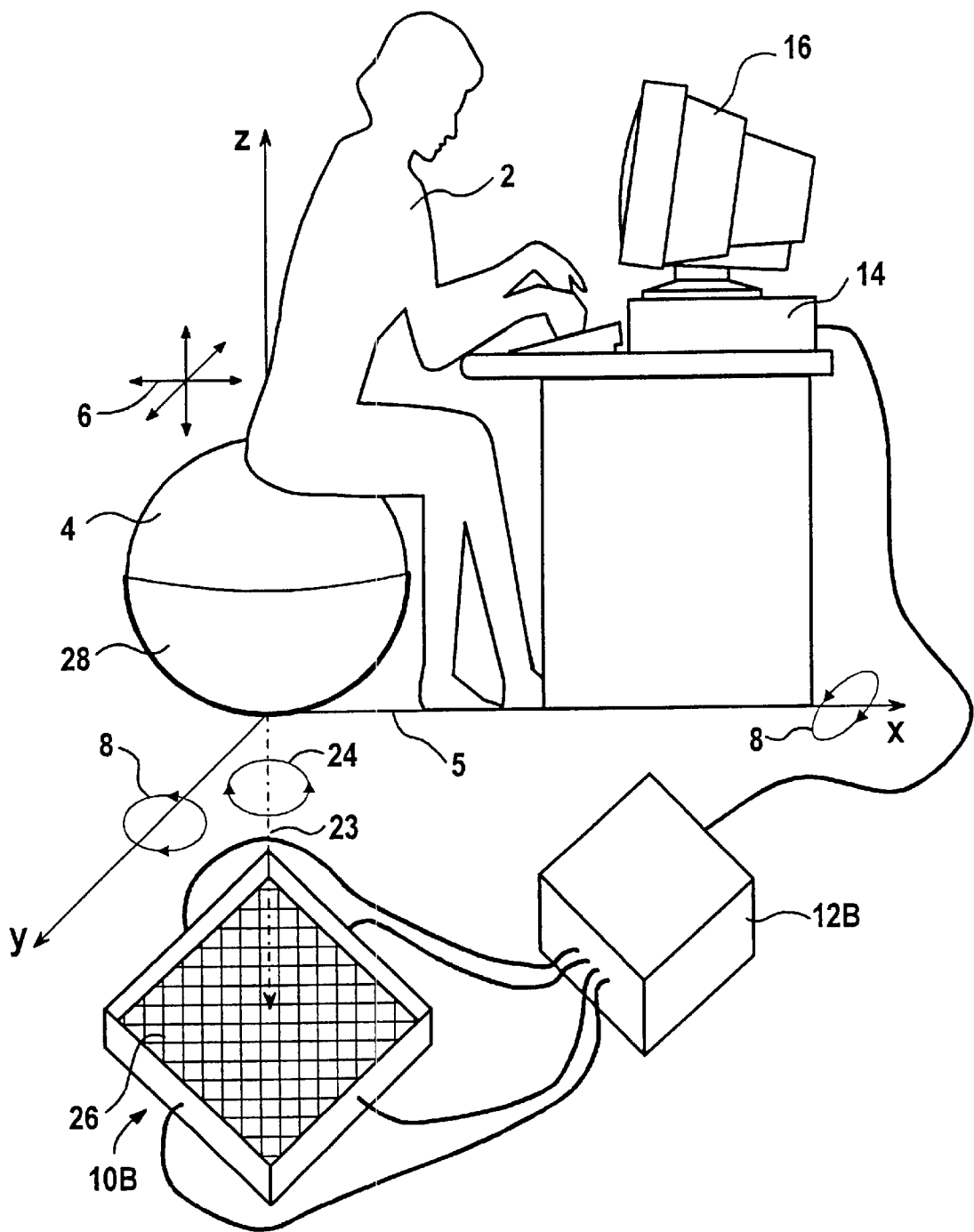
Figure 4:
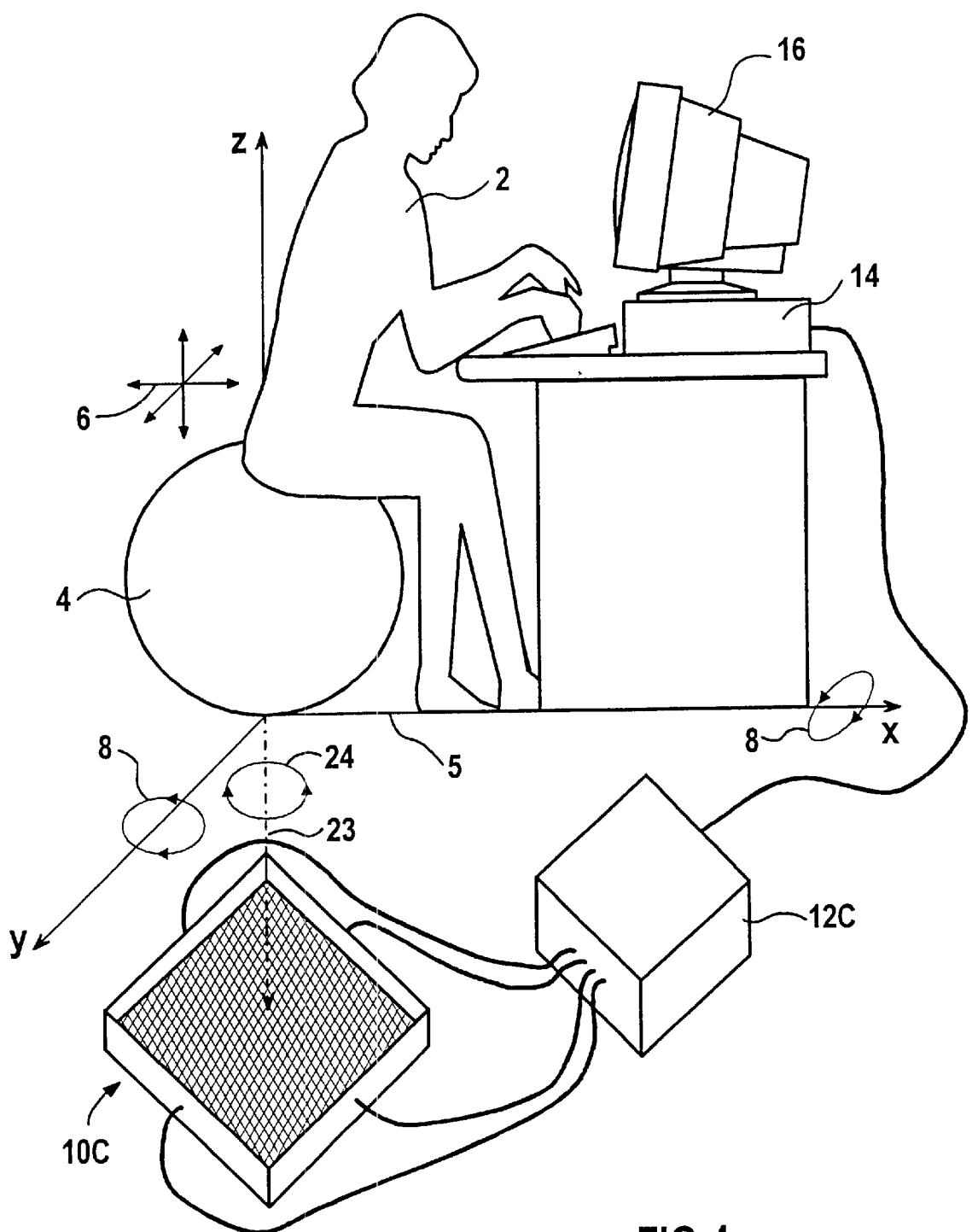
Figure 5:
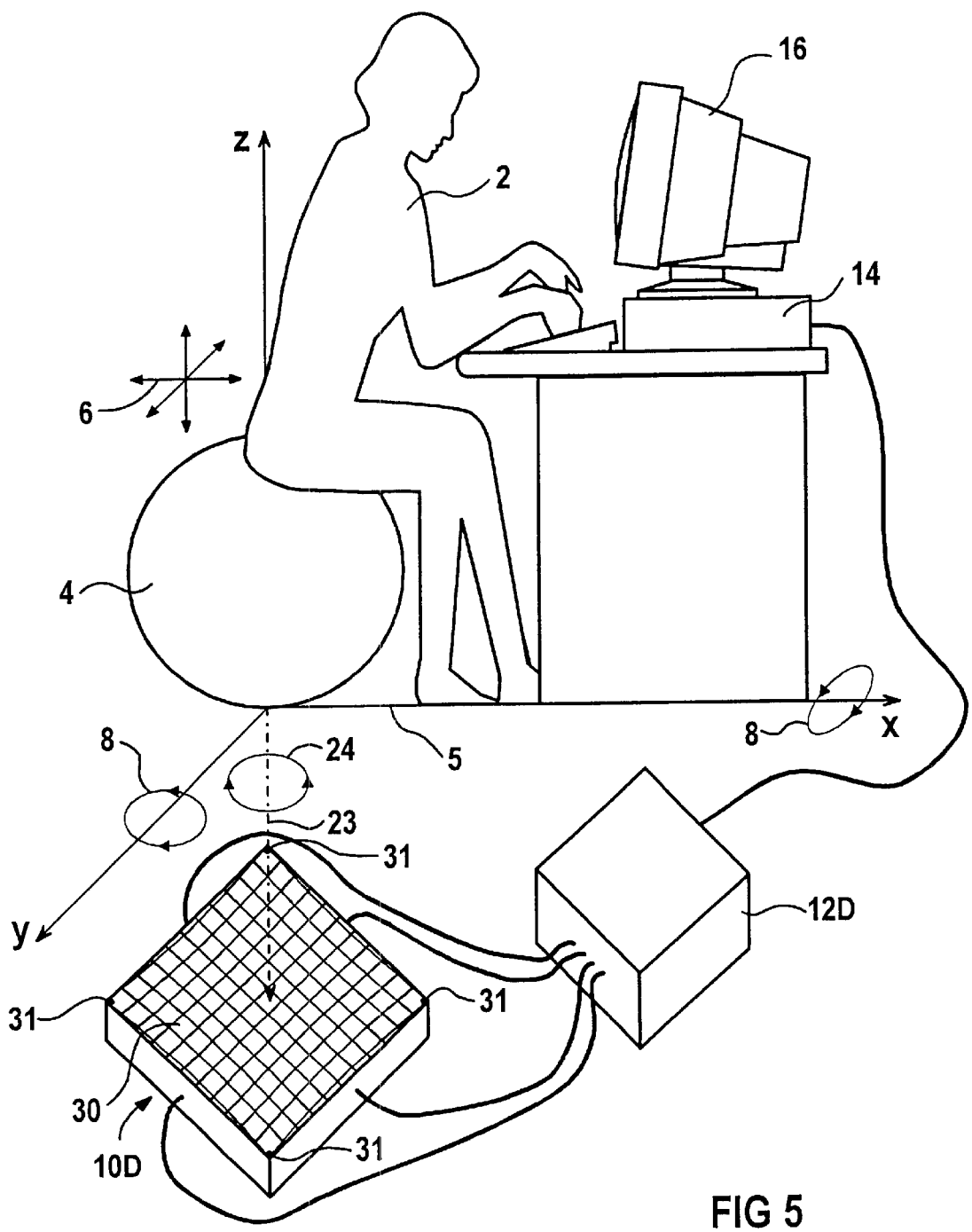
Figure 6:
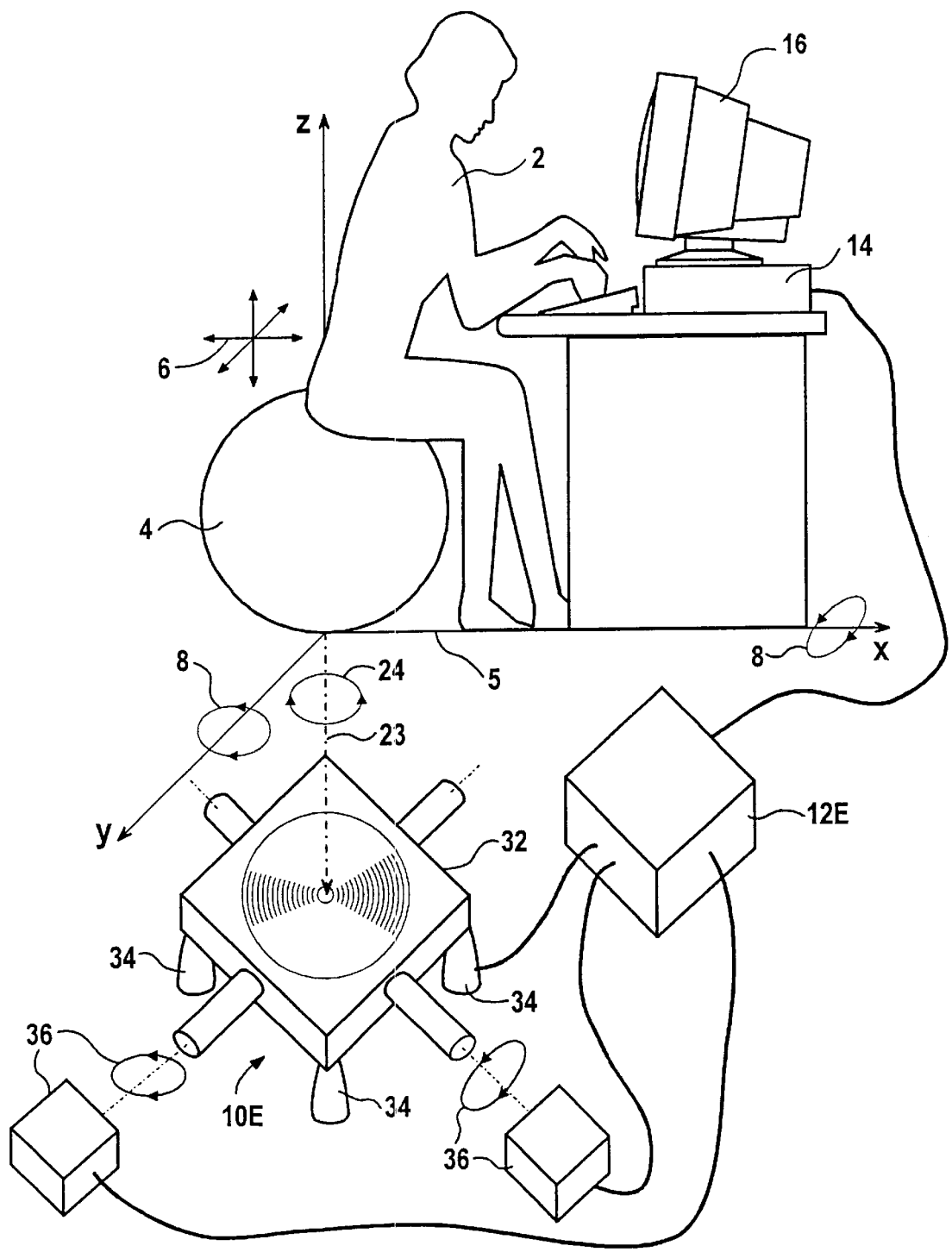
Figure 7:
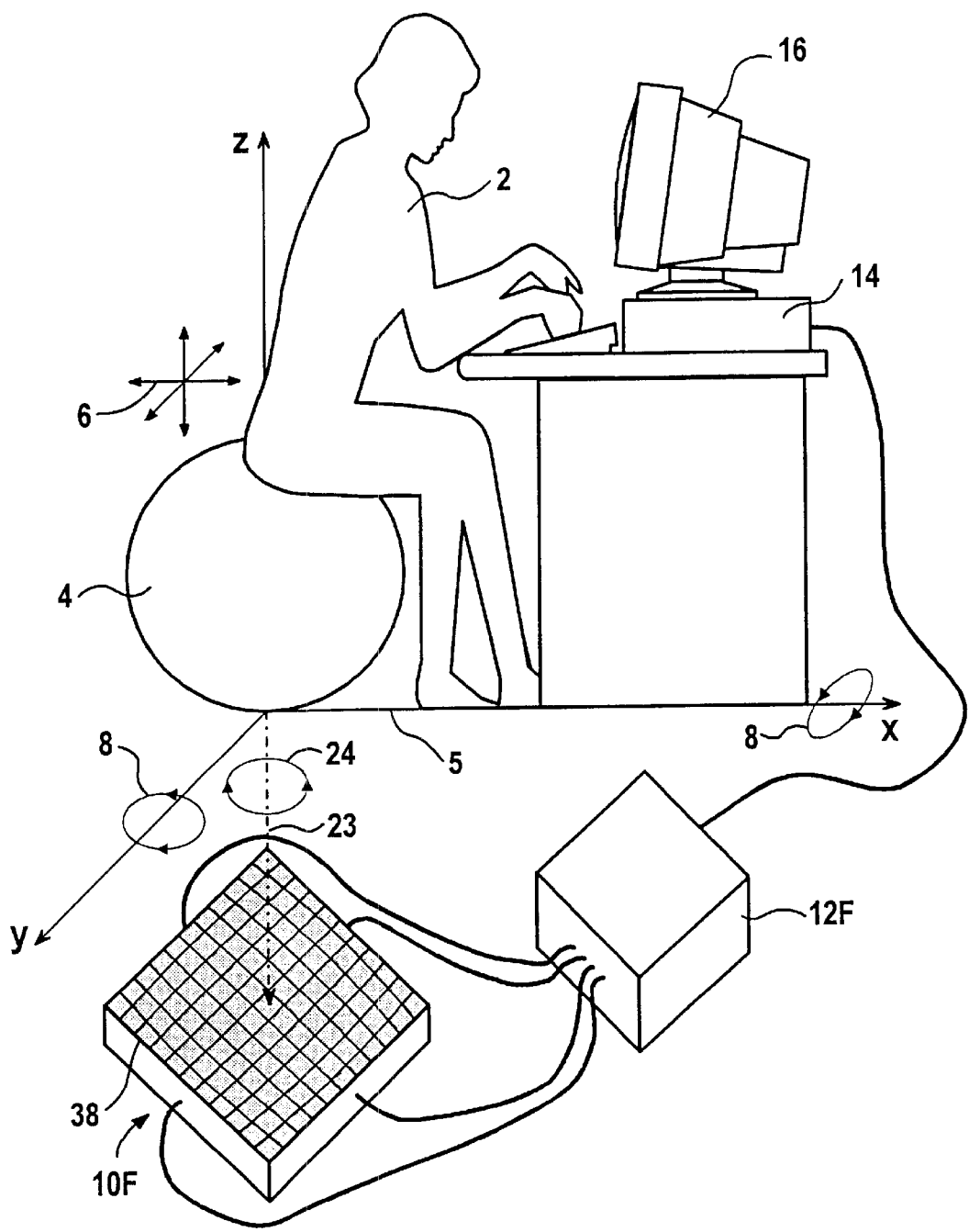
Figure 8:
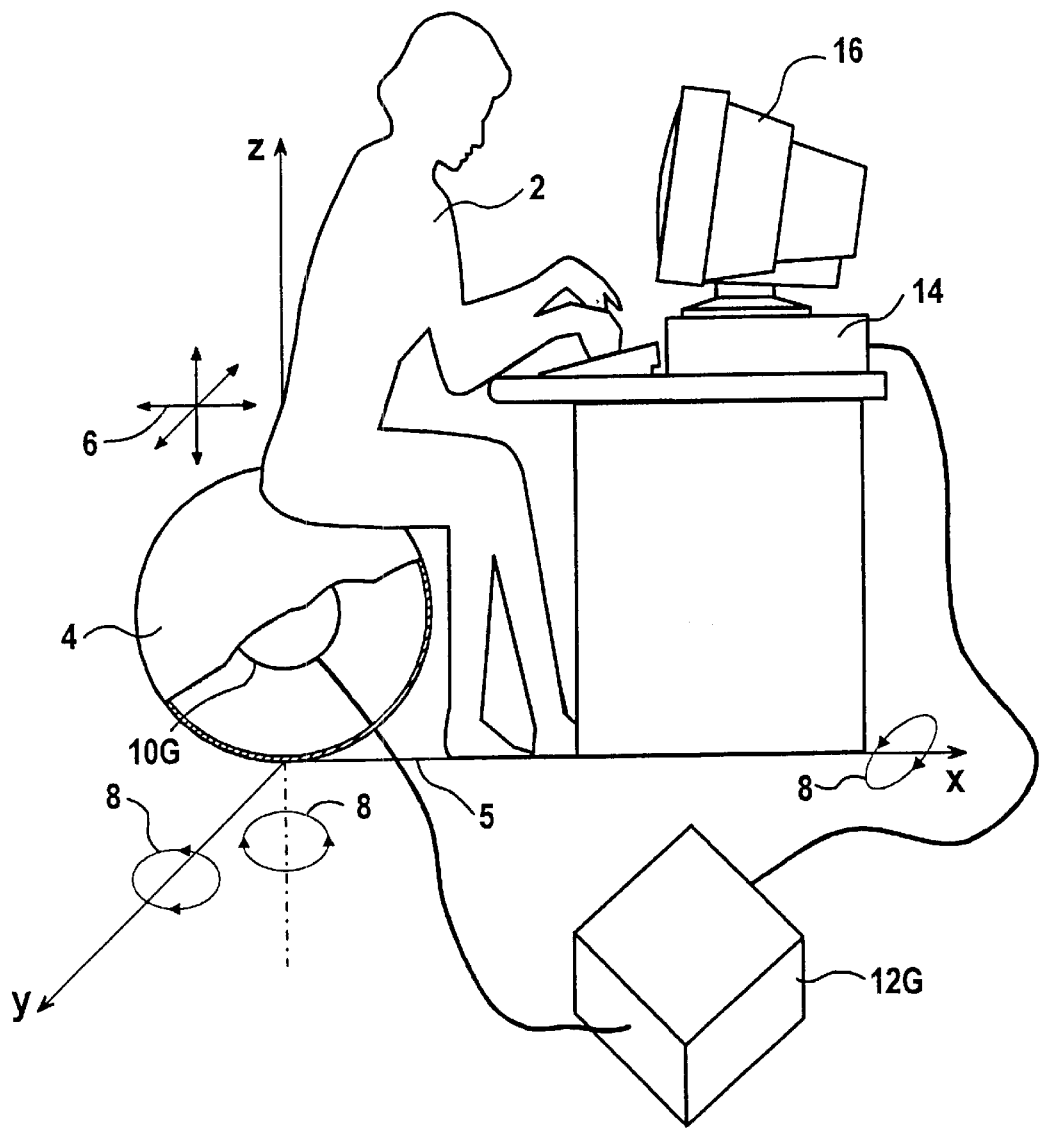
Figure 9:
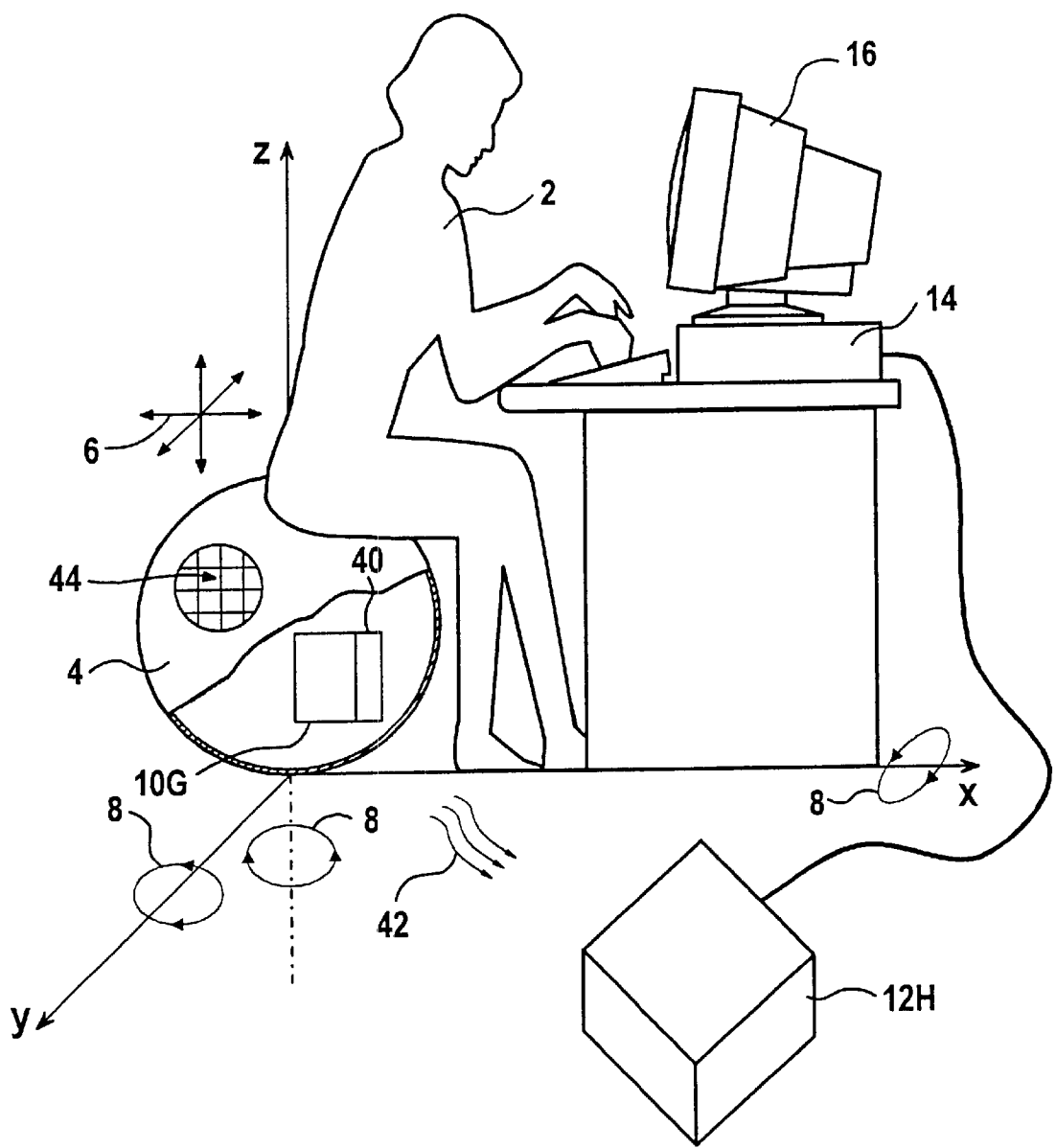
Figure 10:
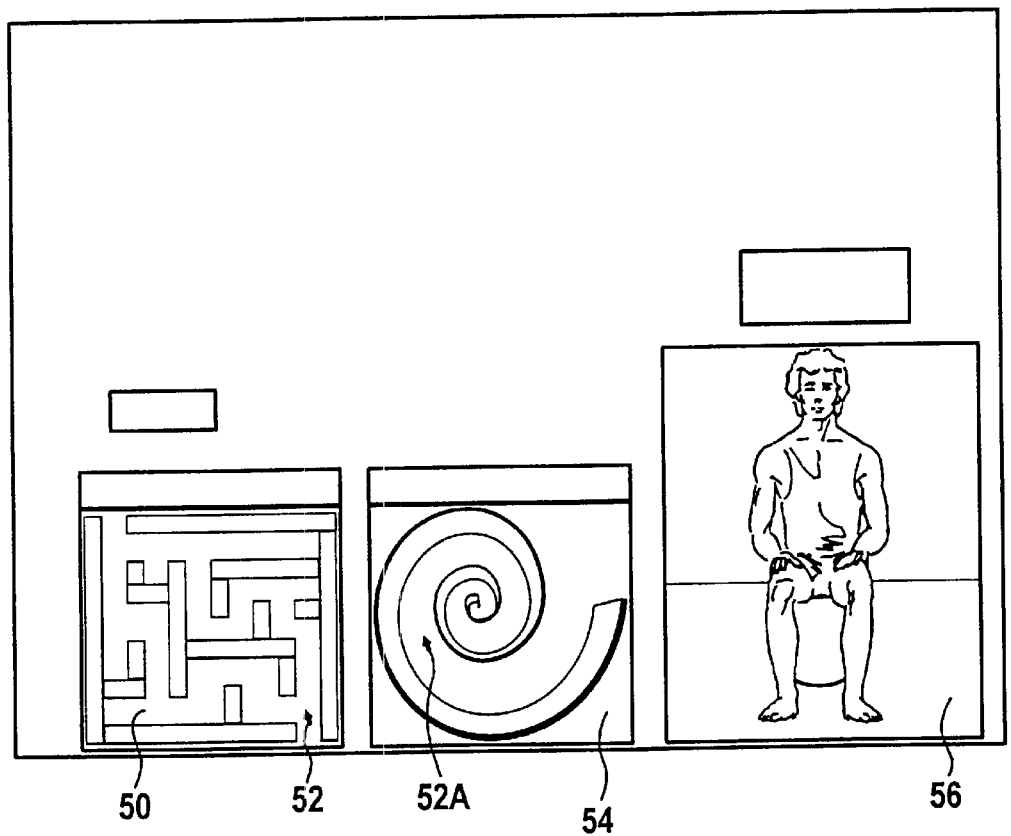

Embodiments of the invention are explained below, based on nine figures, in which:

FIG. 1 shows, in a general illustration, the essential units of a device for training body parts of a person in a sitting position, FIG. 2 shows a first device for training body parts with a light grid system as the sensor unit, FIG. 3 shows a second device for training body parts with an electric contact matrix as the sensor unit, FIG. 4 shows a third device for training a body part with a pressure contact matrix as the sensor unit, FIG. 5 shows a fourth device for training a body part having a net in the sensoric conception that is fastened in at least three fastening points, FIG. 6 shows a fifth device for training body parts with a movably supported plate within the sensoric conception, FIG. 7 shows a sixth device for training body parts with a sensitive mat as the sensor unit, FIG. 8 shows a seventh device for training body parts with a gyroscope as the sensor unit, FIG. 9 shows an eighth device with a wireless transmission of the movement signals, and FIG. 10 shows an illustration of a monitor image with visual specifications of desired movements.

FIG. 1 shows the principle of the arrangement of the device for training body parts of a human being or a person 2 in a sitting position. The person 2 sits on a conventional medical ball seat 4 in such a manner that she supports herself with her feet on the ground. The point of origin of a three-dimensional system of coordinates 5 lies in the contact point of the ball seat 4 with its seat-engaging surface, which, in this case, essentially corresponds to the plane fixed by the coordinates x and y. The person 2 can perform movements on the ball seat 4 in all three space coordinate directions x, y and z, as illustrated by an arrow cross 6. These movements 6, except for the vertical movement in the z-direction, are converted by the ball seat 4 into rolling movements, which can be presented as rotary movements around the x, y and z axis. This is symbolized by circles with arrows 8. If the ball seat 4 is used as the seat device, for instance, the rotary movements 8 effect translational motions. The location change of the ball seat 4 is measured by a sensor arrangement 10 with high accuracy and location resolution, e.g., corresponding to the resolution of a monitor with approx. 1200×800.

The sensor arrangement 10 is connected to an evaluation unit 12, which processes the sensor responses triggered by the movements and outputs them as digitized or also analog signals. The evaluation unit 12 may optionally also comprise a power supply for the sensor arrangement 10. The evaluation unit 12 is connected to a computer 14, which controls a cursor on a monitor 16 based on the movement signals. Simultaneously with the cursor, a path is specified for the cursor on the monitor 16. The person 2 must now, in a sitting position, move the cursor along the specified path through movements on the ball seat, as will be described below in connection with FIG. 10.

A first practical implementation of the sensor concept is shown in FIG. 2, in a partially exploded illustration. A sensor arrangement 10A comprises a light grid system 20, which is created by affixing suitable light barriers to exterior walls 22 of the sensor arrangement 10A. The ball seat is moved within the light grid system 20, which is illustrated by an arrow 23. Multi-dimensional movement and weight-generated positions and/or position changes of the seat device 4 result in shadowing of the corresponding light barriers. The signals that are generated in this manner are converted, with a corresponding evaluation unit 12A, into a digital protocol format. The rotation of the seat device 4 around the z-axis is detected with a rotation sensor, symbolized by a circle 24 with arrowheads, and also routed, via the evaluation unit 12A, to the computer 14. The person 2, in this case, additionally operates an input keyboard during the movement training.

In the conception presented in FIG. 3 an electrical contact matrix is used for the position and movement detection of the seat device 4. A sensor arrangement 10B, which is implemented in this manner comprises an electrical contact matrix 26. The surface of the seat device 4 that is located within the contact area of the contact matrix 26 is coated with an electrically conductive layer 28. By contact closure (arrow 23) of the conductive layer 28 with the contact matrix 26, movement and location signals are generated which, in turn, are converted by the evaluation unit 12B into a digital protocol format. Rotations of the ball seat 4 around the vertical z-axis are again detected, as in the previous embodiment, with a rotation sensor, e.g., a gyroscope, and routed to the computer in digital form.

In the sensor conception illustrated in FIG. 4, a sensor arrangement 10C with a contact matrix is used, similar to the above-described sensor conception, to detect the multi-dimensional position and/or position change of the seat device 4. Here, the contact matrix is designed as a pressure-contact matrix, which closes corresponding contacts when a pressure force acts upon it. A corresponding protocol format is calculated by means of the evaluation unit 12C The conception shown in FIG. 5 uses a sensor arrangement 10D with a net 30, which is secured in at least three fastening points 31—here in the four corner points of the sensor arrangement 10D. At the fastening points 31, path and/or pressure sensors are provided, which convert the multi-dimensional movement and weight-generated position and/or position change of the seat device 4 supported on same with the aid of an appropriate evaluation unit 12D into a protocol format that can be read by the computer 14. Here again, a rotation sensor 24 is additionally provided to detect the rotary movement around the z-axis.

With the sensor conception shown in FIG. 6 a sensor arrangement 10E comprises a rigid plate 32, which is elastically supported in at least three points 34. The plate surface, which serves as a support surface for the seat device 4, may be designed level or also concave. The concave design has the advantage that the movement toward the edge is stabilized. Tilting motions of the plate are detected with two rotation sensors 36. The rotation sensor 24 is additionally provided to detect the rotary movement of the seat device 4 around the vertical z axis. The rotary movements are converted by the evaluation unit 12E into a corresponding digital and computer-compatible format.

FIG. 7 shows, as* a sensor arrangement 10F with a sensor mat, which acquires the movement changes by means of a sensitive mat 38. The signals that are transmitted by the mat 38 are converted by an evaluation unit 12F into a computer-compatible format.

*Translator's note: this is a literal translation of the respective part of the German sentence, which is either incomplete or contains an extraneous "as" (German: "als").

The design of the device for training body parts sketched in FIG. 8 detects movements and/or movement changes of the ball seat 4 by means of a sensor arrangement 10G that is provided inside or on the ball. Here, the sensor arrangement 10G is attached within the ball seat 2**, with the ball seat 4 shown in a partially cut open illustration. The sensor arrangement 10G utilizes the Coriolis forces that occur during movements and movement changes, and/or relativistic transit-time effects of light routed through appropriately arranged fiber glass lines. The dependence of the Sagnak effect on movements and/or movement changes can also be used to measure the movement. Modified vibrating forks, for instance, or modified gyroscopes are used. The inclination and/or rotation of the seat device 4 in the dimensional space influences the above effects and generates corresponding signals, which are converted, by means of an evaluation unit 12G, into signals proportional to the movements.

**Translator's note: this is a typographical error in the German-language document. In FIG. 8, the ball seat is marked with the reference numeral 4.

The sensor concept sketched in FIG. 9 also uses sensors 10G provided on or inside the ball seat, however, they are connected via a transmitter 40 for a wireless signal transmission 42 of the sensor responses to an evaluation unit 12H. The power supply may be provided, e.g., in the form of solar cells 44, which are arranged on an outer surface of the seat device 4.

FIG. 10 shows a graphic image, which is generated by the computer 14 and displayed on the monitor 16. The graphic image comprises a first specified movement 50 in the form of a labyrinth. A cursor, which is shown simultaneously with the specified movement 50, or a moveable visual indicator 52, is to be led through the labyrinth 50 by the person 2 undergoing therapy, by means of corresponding movements on the seat device 4. The movements of the seat device 4 are detected by the sensor unit 10 and converted by the computer 14 into corresponding control signals for the cursor 52. If the cursor 52 is led to the target without mistake, e.g., without touching the sidewalls that delimit the path, a success signal appears on the monitor 16. The person 2, who is to perform the movement training, is offered an alternative second specified movement 54 in the form of a spiral. Here, a cursor 52A is to be led to the center point along the specified path area. As opposed to the labyrinth 50, with this specified movement 54, the training focusses on circular motions.

If the training person 2 is additionally taped with a video camera, a fade-in picture 56 with a corresponding image may be displayed on the monitor 16, when activated, in addition to the specified movement 50 or 54.

What is claimed is:

1. A device for training body parts of a person in a sitting position comprising:
   a) a seat device to be supported by a support surface, said seat device having a seating surface upon which a person is to be seated;
   b) display means for displaying to the person a desired movement to be performed by the person;
   c) a sensor arrangement for generating movement signals corresponding to a movement of the person on said seating surface, said sensor arrangement being connected to said seat device; and
   d) a processing unit connected to said sensor arrangement for generating a presentation of the movement from said movement signals, said presentation of the movement being displayed by said display means.

2. The device according to claim 1, wherein the sensor arrangement comprises a multitude of sensor elements, which are arranged on a surface.

3. The device according to claim 1, wherein the sensor arrangement comprises a plate-shaped rigid element, said plate-shaped element is mounted in a tilt mechanism, and the tilt mechanism comprises at least two rotation sensors.

4. The device according to claim 3, wherein the plate-shaped element has a concave surface.

5. The device according to claim 1, wherein the sensor arrangement comprises a net-like element and a plurality of sensors, said net-like element is secured along its edges in at least three fastening points, and said sensors are provided at the fastening points.

6. The device according to claim 1, further comprising at least one gyroscope connected to said seat device to detect a rotary movement of said seat device.

7. The device according to claim 6, further comprising a transmitter connected to said gyroscope for a wireless transmission of the rotary movement signals.

8. The device according to claim 1, wherein said seat device comprises an electric energy source.

9. A method for training body parts of a person in a sitting position comprising the following steps:
   a) providing a seat device having a seating surface thereon;
   b) seating a person on said seating surface;
   c) specifying to the person desired movements to be performed by the person;
   d) measuring movements of the person on the seating surface by means of a sensor arrangement and generating corresponding movement signals;
   e) generating a presentation of the movements from said movement signals by means of a processing unit; and
   f) displaying said presentation by display means.

10. The method of claim 9 wherein the display means comprise a monitor.

11. The method of claim 10, wherein the presentation of the movements takes place in the form of a cursor, the location of which on the monitor is derived from said movement signals.

12. The method of claim 10, wherein the desired movements are specified in the form of a desired path to be traveled by a cursor on the monitor.

13. The method of claim 10, wherein a presentation of the desired movements takes place on the same monitor that displays the movements of the person.

14. The method of claim 9, wherein the seat device comprises a ball seat and movements of the sitting person is transmitted via the ball seat to the sensor arrangement.

15. The method of claim 9, wherein the movement signals are generated quasi-continuously.

16. The method of claim 9, further comprising forming a quality signal from the desired movements and the movement signals, as a measure for the correspondence between the desired movements and the measured movements.

17. A device for training body parts of a person in a sitting position comprising:
   a) a seat device to be supported by a support surface, said seat device being designed as a ball seat upon which a person is to be seated;
   b) display means for displaying to the person a desired movement to be performed by the person;
   c) a sensor arrangement for generating movement signals corresponding to a movement of the person on said ball seat, said sensor arrangement being connected to said seat device; and
   d) a processing unit connected to said sensor arrangement for generating a presentation of the movement from said movement signals, said presentation of the movement being displayed by said display means.

18. The device according to claim 17, wherein the sensor arrangement comprises a multitude of sensor elements, which are arranged on a surface.

19. The device according to claim 17, wherein the sensor arrangement comprises a plate-shaped rigid element, said plate-shaped element is mounted in a tilt mechanism, and the tilt mechanism comprises at least two rotation sensors.

20. The device according to claim 19, wherein the plate-shaped element has a concave surface.

21. The device according to claim 17, wherein the sensor arrangement comprises a net-like element and a plurality of sensors, said net-like element is secured along its edges in at least three fastening points, and said sensors are provided at the fastening points.

22. The device according to claim 17, further comprising at least one gyroscope connected to said seat device to detect a rotary movement of said seat device.

23. The device according to claim 22, further comprising a transmitter connected to said gyroscope for a wireless transmission of the rotary movement signals.

24. The device according to claim 17, wherein the seat device comprises an electric energy source.

* * * * *